United States Patent [19]

Kleemiss et al.

[11] Patent Number: 5,767,326

[45] Date of Patent: Jun. 16, 1998

[54] PROCESS FOR PREPARING HYDROXYMETHYLCYCLOPROPANE

[75] Inventors: Wolfgang Kleemiss, Haltern; Marcel Feld, Cologne, both of Germany

[73] Assignee: Huels Aktiengesellschaft, Marl, Germany

[21] Appl. No.: 813,593

[22] Filed: Mar. 7, 1997

[30] Foreign Application Priority Data

Mar. 7, 1996 [DE] Germany ............... 196 08 852.6

[51] Int. Cl.$^6$ ........................................ C07C 27/10
[52] U.S. Cl. ........................................... 568/700
[58] Field of Search .............................. 568/700, 839

[56] References Cited

U.S. PATENT DOCUMENTS 4,720,597  1/1988  Otte et al. .

5,345,005  9/1994  Thakur et al. .
5,475,151  12/1995  Liang et al. .

FOREIGN PATENT DOCUMENTS 9210290  6/1992  WIPO .

*Primary Examiner*—Gary Geist
*Assistant Examiner*—Karl J. Puttlitz, Jr.
*Attorney, Agent, or Firm*—Oblon, Spivak, McClelland, Maier & Neustadt, P.C.

[57] ABSTRACT

A process for preparing hydroxymethylcyclopropane, in which formylcyclopropane is hydrogenated over copper chromite, zinc chromite and/or copper/zinc catalysts. The process may be batchwise or continuous.

13 Claims, No Drawings

PROCESS FOR PREPARING HYDROXYMETHYLCYCLOPROPANE

BACKGROUND OF THE INVENTION

1. Field of the Invention

The invention relates to a process for preparing hydroxymethylcyclopropane (a.k.a. cyclopropylmethanol) by catalytic hydrogenation of formylcyclopropane. Hydroxymethylcyclopropane is an important intermediate for, e.g., the production of bactericides, fungicides, herbicides, and insecticides.

2. Discussion of the Background

Hydroxymethylcyclopropane can be prepared by reducing cyclopropanecarboxylic acid with lithium alanate (Beilstein, Handbuch der Organischen Chemie, E6 IV,4). In another known process for preparing hydroxymethylcyclopropane, cyclopropanecarboxylic acid is reacted with organometallic compounds in the presence of electrophilic compounds (U.S. Pat. Nos. 4,085,173; 4,085, 273; 4,054,480; 3,998,889; and 3,959,324). Hydroxymethylcyclopropane can also be prepared by anodic oxidation of cyclobutanecarboxylic acid (J. Am. Chem. Soc., 82, 2645–2646 (1960)). All of these processes are laborious and give only moderate yields. These processes also require complex and expensive chemicals, some of which are unsafe to handle.

Catalytic hydrogenation of cyclopropanecarboxylic esters (DE-A1-35 38 132) presents a significant advance over the above processes. The catalyst in this process is zinc chromite; under similar conditions copper chromite results in a 59% yield of n-butanol, due to opening of the cyclopropane ring. A disadvantage of this process is the relatively expensive starting material, which is prepared in a three-stage synthesis from butyrolactone (DE-A-29 41 211, EP-A-0 220 412).

SUMMARY OF THE INVENTION

Accordingly, one object of this invention is to provide a novel method for preparing hydroxymethylcyclopropane from a different, more easily obtainable starting material in good yield and with high selectivity.

Another object is to provide a novel method of preparing hydroxymethylcyclopropane in good yield and with high selectivity in a batchwise manner or continuous manner.

These objects are achieved by hydrogenating formylcyclopropane over zinc chromite, copper chromite and/or copper/zinc catalysts.

DETAILED DESCRIPTION OF THE PREFERRED EMBODIMENTS

The noble metal catalysts commonly used in the art for converting a carbonyl function to a hydroxyl function, e.g., palladium or platinum, are inappropriate for hydrogenating formylcyclopropane. These catalysts lead to open-chain compounds due to opening of the cyclopropane ring (Houben-Weyl, Methoden der Organischen Chemie, IV/1c, 405 [1980]). For example, cyclopropyl methyl ketone is converted directly to the open-chain compound 2-pentanone under hydrogenating conditions over palladium (J. Org. Chem. 36, 383 [1971]).

Surprisingly, the process according to the present invention, using copper chromite or copper/zinc as catalyst, produces yields of over 90% of hydroxymethylcyclopropane, particularly since hydrogenation of cyclopropanecarboxylic esters over copper chromite leads predominantly to n-butanol via ring opening, as mentioned above. It is also surprising that even at temperatures below 40° C., hydrogenation over copper chromite is also successful, with complete conversion, very good yields, and correspondingly higher selectivity with respect to the product hydroxymethylcyclopropane.

A further advantage of the process according to the invention over the hydrogenation of cyclopropanecarboxylic esters is that no alcohol is formed, which facilitates work up of the hydrogenation mixture.

Formylcyclopropane can be prepared from 1,4-butanediol via 2,3-dihydrofuran as intermediate (U.S. Pat. No. 4,274, 238) or from 1,3-butadiene via the intermediates 1,3-butadiene monoepoxide, 2,5-dihydrofuran, and 2,3-dihydrofuran (U.S. Pat. No. 5,138,077, U.S. Pat. No. 5,315, 019, DE-A1-38 03 987). These are catalytic processes which produce stoichiometric yields without auxiliary reagents, and therefore yield inexpensive formylcyclopropane despite the plurality of stages.

The catalysts used in the present invention are known, and a number are commercially available. Suitable zinc chromite catalysts generally contain from 40 to 80%, preferably 55 to 65% by weight of ZnO and from 20 to 40%, preferably 25 to 35% by weight of $Cr_2O_3$, and have a loss on ignition of from 10 to 20% by weight. An example of an appropriate zinc chromite catalyst is the catalyst S5-10 from BASF AG. The zinc chromite catalysts can also comprise other metal oxides, without any reduction in the desired activity, e.g., from 1 to 20% by weight, based on the sum of ZnO and $Cr_2O_3$, of oxides of aluminum, iron, titanium, manganese, rare earth metals, alkali metals, or alkaline earth metals.

Suitable copper chromite catalysts generally contain from 30 to 60%, preferably 40 to 50% by weight of CuO and from 30 to 60%, preferably 40 to 50% of $Cr_2O_3$ and have a loss on ignition of from 10 to 20% by weight. An example of an appropriate copper chromite catalyst is the Mallinckrodt catalyst E406TU. The copper chromite catalysts can also comprise other metal oxides without any reduction in the desired activity, e.g., from 1 to 20% by weight, based on the sum of CuO and $Cr_2O_3$, of oxides of aluminum, iron, titanium, manganese, rare earth metals, alkali metals, or alkaline earth metals.

Suitable copper/zinc catalysts can be prepared, for example, by coprecipitation from solutions comprising copper salts and zinc salts, washing of the isolated precipitate with water, drying of the isolated precipitate, and conversion of the resulting oxide form of the catalyst into the hydrogenation-active, reduced form by heating in a hydrogen atmosphere. In the oxide form, the copper/zinc catalysts generally contain from 30 to 50%, preferably 35 to 45% by weight of CuO and from 20 to 40%, preferably 25 to 35% by weight of ZnO, and have a loss on ignition of from 20 to 40% by weight. The copper/zinc catalysts may comprise other metal oxides without any reduction in the desired activity, e.g., from 1 to 20% by weight, based on the sum of CuO and ZnO, of oxides of aluminum, iron, titanium, manganese, rare earth metals, alkali metals, or alkaline earth metals.

The oxide form of the catalyst can be converted into the hydrogenation-active, reduced form by treatment with hydrogen at, e.g., a temperature of from 200° to 400° C., under atmospheric pressure or at elevated pressure, e.g., 50 bar.

Hydrogenation according to the invention is advantageously carried out at from 20° to 250° C., preferably 30° to 220° C., more preferably 50° to 180° C., even more preferably 80° to 150° C. Below 20° C., the hydrogenation rate of even the most active catalysts is low. Above 250° C., there is a rapid increase in decomposition reactions, even with appropriately short contact times. The optimum temperature range for zinc chromite catalysts is from 180° to 220 ° C., the optimum temperature range for copper chromite catalysts is from 30° to 50° C., and the optimum temperature range for copper/zinc catalysts is from 80° to 150° C.

In the process according to the invention the hydrogen pressure is generally from 10 to 350 bar, preferably from 100 to 320 bar, more preferably from 150 to 300 bar, irrespective of the catalyst used.

In the process according to the invention the formylcyclopropane can be employed without solvents or diluents. If desired it is possible to use, e.g., alcohols, ethers, alkanes, aromatics and alkylaromatics as solvents or diluents as well. Owing to the surprisingly high thermal stability of hydroxymethylcyclopropane, this target product may also be used as solvent or diluent.

The process according to the invention can be carried out in a batchwise or continuous process, preferably in a continuous process.

In batchwise operation, a pressure autoclave with temperature regulation is generally used, preferably with a pulverulent catalyst in a fluidized (liquid or slurry) state. An initial mixture is brought to the reaction temperature, and hydrogen is injected until the pressure remains constant. Hydrogenation reaction time in this mode is about 3 to 10 hours.

In continuous operation, a fixed (trickle) bed process is preferably employed. In such a trickle bed process, the starting material is allowed to trickle over the catalyst bed, the catalyst being in the form of coarse particles in a heatable reaction tube, while passing hydrogen through the bed in cocurrent or countercurrent. Preferably, excess hydrogen is recirculated. In general, depending on the catalyst and temperature, the liquid hourly space velocity (LHSV) is generally from 0.1 to 0.75 h$^{-1}$.

In both cases the reaction product is preferably worked up by continuous or discontinuous fractional distillation.

EXAMPLES

Example I

A 400 ml vertical tube reactor was charged with copper chromite catalyst (E406TU from Mallinckrodt) particles of particle size of from 5 to 10 mm. 200 ml of formylcyclopropane per hour were trickled over the catalyst, while the temperature in the reaction tube was held at 40° C. At the same time, hydrogen was passed through the tube in cocurrent under a pressure of 285 bar. The LHSV was 0.125 h$^{-1}$.

The hydrogenation product was distilled through a 20 cm packed column to yield, based on the hydrogenation mixture:

| Initial fraction | 5% by weight |
|---|---|
| Hydroxymethylcyclopropane | 91% by weight |
| Final fraction | 4% by weight |

The conversion of formylcyclopropane was >99%, and the yield of hydroxymethylcyclopropane corresponds to 91% of theory.

Example 2

Formylcyclopropane was hydrogenated by the procedure of Example 1 over zinc chromite catalyst (S5-10 from BASF AG) particles with a particle size of from 5 to 10 mm. The temperature was 200° C. and the hydrogen pressure was 285 bar.

The hydrogenation discharge was distilled through a 20 cm packed column to yield, based on the hydrogenation mixture:

| Initial fraction | 9% by weight |
|---|---|
| Hydroxymethylcyclopropane | 61% by weight |
| Final fraction | 30% by weight |

The conversion of formylcyclopropane was >99%, and the yield of hydroxymethylcyclopropane was about 61%.

Example 3

Formylcyclopropane was hydrogenated by the procedure of Example 1 over copper/zinc catalyst particles of particle size of from 5 to 10 mm. The catalyst had, in the oxide form, the following composition: 42.2% by weight of CuO, 26.9% by weight of ZnO, 30.9% by weight loss on ignition. The catalyst was placed in the reactor in this form and was converted into the reduced, active form by passing hydrogen over the catalyst for 6 hours under a pressure of 1 bar and at a temperature of 250° C. The formylcyclopropane was hydrogenated at a temperature of 120° C. under a hydrogen pressure of 285 bar.

The hydrogenation discharge was distilled through a 20 cm packed column to yield, based on the hydrogenation mixture:

| Initial fraction | 5% by weight |
|---|---|
| Hydroxymethylcyclopropane | 90% by weight |
| Final fraction | 5% by weight |

The conversion of formylcyclopropane was >99%, and the yield of hydroxymethylcyclopropane was about 90%.

This application is based on DE 196 08 852.6, filed with the German Patent Office on Mar. 7, 1996, the entire contents of which are incorporated herein by reference.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A process for preparing hydroxymethylcyclopropane, comprising the step of hydrogenating formylcyclopropane over a catalyst comprising one selected from the group consisting of copper chromite, zinc chromite, and copper/zinc, or mixtures thereof.

2. The process of claim 1, wherein the temperature of the hydrogenating step is from 20° to 250° C.

3. The process of claim 2, wherein the catalyst is zinc chromite and the temperature is from 180° to 220° C.

4. The process of claim 3, wherein the zinc chromite catalyst contains from 40 to 80% by weight of ZnO and from 20 to 40% by weight of $Cr_2O_3$.

5. The process of claim 2, wherein the catalyst is copper chromite and the temperature is from 30° to 50° C.

6. The process of claim 5, wherein the copper chromite contains from 30 to 60% by weight of CuO and from 30 to 60% of $Cr_2O_3$.

7. The process of claim 2, wherein the catalyst is copper oxide/zinc and the temperature is from 80° to 150° C.

8. The process of claim 7, wherein the copper oxide/zinc catalyst contains from 30 to 50% CuO and from 20 to 40% of ZnO.

9. The process of claim 1, wherein the catalyst further comprises from 1 to 20% by weight of oxides of aluminum, iron, titanium, manganese, rare earth metals, or alkaline earth metals.

10. The process of claim 1, wherein the hydrogenating step is carried out at a hydrogen pressure of from 10 to 350 bar.

11. The process of claim 10, wherein the hydrogenating step is carried out at a hydrogen pressure of from 100 to 320 bar.

12. The process of claim 10, wherein the hydrogenating step is carried out at a hydrogen pressure of from 150 to 300 bar.

13. The process of claim 1, wherein the hydrogenating step is carried out in a fluid bed or trickle bed.

* * * * *